United States Patent
Boulnois et al.

(10) Patent No.: US 8,920,309 B2
(45) Date of Patent: Dec. 30, 2014

(54) PICTURE IN PICTURE CLIP APPLIER VIDEO SYSTEM

(75) Inventors: Jean-Luc Boulnois, Boston, MA (US); Christopher Devlin, Wakefield, MA (US)

(73) Assignee: Microline Surgical, Inc., Beverly, MA (US)

( * ) Notice: Subject to any disclaimer, the term of this patent is extended or adjusted under 35 U.S.C. 154(b) by 1025 days.

(21) Appl. No.: 12/723,007

(22) Filed: Mar. 12, 2010

(65) Prior Publication Data

US 2011/0224485 A1     Sep. 15, 2011

(51) Int. Cl.
| | | |
|---|---|---|
| A61B 1/00 | (2006.01) | |
| A61B 1/05 | (2006.01) | |
| H04N 5/45 | (2011.01) | |
| A61B 17/128 | (2006.01) | |
| A61B 1/313 | (2006.01) | |
| A61B 19/00 | (2006.01) | |

(52) U.S. Cl.
CPC .......... *H04N 5/45* (2013.01); *A61B 2019/5206* (2013.01); *A61B 19/5212* (2013.01); *A61B 1/05* (2013.01); *A61B 17/1285* (2013.01); *A61B 1/3132* (2013.01)
USPC ........................................................ 600/104

(58) Field of Classification Search
USPC ........................................................ 600/104
See application file for complete search history.

(56) References Cited

U.S. PATENT DOCUMENTS

| | | | |
|---|---|---|---|
| 4,447,120 A * | 5/1984 | Borsuk ......................... | 385/136 |
| 4,782,819 A | 11/1988 | Adair | |
| 5,125,056 A * | 6/1992 | Hughes et al. .................. | 385/59 |
| 5,287,845 A | 2/1994 | Faul et al. | |
| 5,331,950 A | 7/1994 | Wood, Sr. | |
| 5,394,499 A | 2/1995 | Ono et al. | |
| 5,403,327 A * | 4/1995 | Thornton et al. ............. | 606/143 |
| 5,448,990 A | 9/1995 | De Faria-Correa | |
| 5,498,230 A | 3/1996 | Adair | |
| 5,551,947 A | 9/1996 | Kaali | |
| 5,569,254 A | 10/1996 | Carlson et al. | |
| 5,667,473 A | 9/1997 | Finn et al. | |

(Continued)

FOREIGN PATENT DOCUMENTS

| | | |
|---|---|---|
| JP | 63-131380 | 8/1988 |
| JP | 05-168643 | 7/1993 |

(Continued)

OTHER PUBLICATIONS

Canada Office action, mail date is May 10, 2013.

(Continued)

*Primary Examiner* — Clayton E Laballe
*Assistant Examiner* — Linda B Smith
(74) *Attorney, Agent, or Firm* — Greenblum & Bernstein, P.L.C.

(57) ABSTRACT

An endoscopic video system for visualizing an internal body cavity is provided. The endoscopic video system may include a first instrument and a second instrument. The first instrument may include a light configured to illuminate the cavity, and a first camera configured to capture first images of the illuminated cavity. The second instrument may include a surgical tool configured to perform a surgical procedure, and a second camera configured to capture second images of the illuminated cavity. In addition, the endoscopic video system may further include a video control unit configured to receive the captured first and second images, and a video display configured to display the captured first and second images transmitted from the video control unit.

32 Claims, 3 Drawing Sheets

(56) References Cited

U.S. PATENT DOCUMENTS

| | | | |
|---|---|---|---|
| 5,667,478 A * | 9/1997 | McFarlin et al. | 600/182 |
| 5,690,605 A | 11/1997 | Hamlin et al. | |
| 5,817,013 A | 10/1998 | Ginn et al. | |
| 5,891,013 A | 4/1999 | Thompson | |
| 5,928,137 A | 7/1999 | Green | |
| 5,986,693 A | 11/1999 | Adair et al. | |
| 6,022,313 A | 2/2000 | Ginn et al. | |
| 6,071,233 A | 6/2000 | Ishikawa et al. | |
| 6,139,489 A | 10/2000 | Wampler et al. | |
| 6,159,200 A | 12/2000 | Verdura et al. | |
| 6,221,007 B1 | 4/2001 | Green | |
| 6,277,064 B1 * | 8/2001 | Yoon | 600/114 |
| 6,277,131 B1 | 8/2001 | Kalikow | |
| 6,348,034 B1 | 2/2002 | Thompson | |
| 6,387,043 B1 | 5/2002 | Yoon | |
| 6,419,626 B1 | 7/2002 | Yoon | |
| 6,569,085 B2 | 5/2003 | Kortenbach et al. | |
| 6,636,254 B1 | 10/2003 | Onishi et al. | |
| RE38,445 E * | 2/2004 | Pistl et al. | 606/143 |
| 7,214,183 B2 | 5/2007 | Miyake | |
| 8,128,643 B2 * | 3/2012 | Aranyi et al. | 606/143 |
| 8,292,801 B2 | 10/2012 | Dejima et al. | |
| 2003/0040759 A1 | 2/2003 | de Guillebon et al. | |
| 2003/0176880 A1 | 9/2003 | Long et al. | |
| 2004/0054254 A1 | 3/2004 | Miyake | |
| 2004/0064016 A1 | 4/2004 | Kobayashi et al. | |
| 2005/0004431 A1 | 1/2005 | Kogasaka et al. | |
| 2005/0119523 A1 | 6/2005 | Starksen et al. | |
| 2005/0234297 A1 | 10/2005 | Devierre et al. | |
| 2005/0272975 A1 | 12/2005 | McWeeney et al. | |
| 2005/0277954 A1 * | 12/2005 | Smith et al. | 606/142 |
| 2006/0030751 A1 * | 2/2006 | Uesugi et al. | 600/101 |
| 2006/0058617 A1 | 3/2006 | Sano et al. | |
| 2006/0058624 A1 * | 3/2006 | Kimura | 600/407 |
| 2006/0149129 A1 * | 7/2006 | Watts et al. | 600/113 |
| 2006/0155168 A1 | 7/2006 | Pease | |
| 2006/0190013 A1 | 8/2006 | Menn | |
| 2006/0258955 A1 | 11/2006 | Hoffman et al. | |
| 2007/0049950 A1 | 3/2007 | Theroux et al. | |
| 2007/0161855 A1 | 7/2007 | Mikkaichi et al. | |
| 2007/0179340 A1 | 8/2007 | Jorgensen | |
| 2007/0255100 A1 | 11/2007 | Barlow et al. | |
| 2008/0140090 A1 | 6/2008 | Aranyi et al. | |
| 2008/0154091 A1 | 6/2008 | Dejima et al. | |
| 2008/0221392 A1 | 9/2008 | Jorgensen | |
| 2009/0171159 A1 | 7/2009 | Jorgensen et al. | |
| 2009/0182193 A1 | 7/2009 | Whitman et al. | |
| 2010/0106167 A1 | 4/2010 | Boulnois et al. | |
| 2012/0143002 A1 * | 6/2012 | Aranyi et al. | 600/104 |
| 2013/0225926 A1 * | 8/2013 | Smith et al. | 600/114 |

FOREIGN PATENT DOCUMENTS

| | | |
|---|---|---|
| JP | 5-337119 | 12/1993 |
| JP | 10-314104 | 12/1998 |
| JP | 2000-201943 | 7/2000 |
| JP | 2000-510362 | 8/2000 |
| JP | 2001-517104 | 10/2001 |
| JP | 2004-109222 | 4/2004 |
| JP | 2006-61214 | 3/2006 |
| JP | 2008-155030 | 7/2008 |
| JP | 2009-39243 | 2/2009 |
| JP | 2013-132559 | 7/2013 |
| WO | 2007/078003 | 7/2007 |
| WO | 2009/089539 | 7/2009 |

OTHER PUBLICATIONS

Japan Office action, mail date is Dec. 11, 2012.
Japan Office action, mail date is Mar. 19, 2013.
Japanese Office Action dated Mar. 4, 2014, along with English-language translation thereof.
EPO Official Action dated Oct. 10, 2014.

* cited by examiner

PICTURE IN PICTURE CLIP APPLIER VIDEO SYSTEM

BACKGROUND OF THE INVENTION

1. Field of the Invention

This disclosure relates to an endoscopic video system with picture-in-picture capabilities and an endoscope for use in the endoscopic video system.

2. Description of the Related Art

Traditional endoscopic video systems generally include an endoscope having an objective lens system provided at a distal end of the endoscope that forms an image that can be seen on, for example, a video monitor. In medical applications, the endoscopic video systems are utilized to view images within a closed cavity of a patient. Often these endoscopic video systems can be used in conjunction with various sorts of endoscopic tools to perform a medical procedure. One such tool is a clip applier, which may utilize a clip to grasp and/or crimp/seal tissue by the single hand of an operating surgeon, and is described in commonly-assigned U.S. Patent Publication No. 2003/0040759, U.S. Patent Publication 2007/0049950 and U.S. Pat. No. 6,277,131, the entire contents of each document being expressly incorporated by reference herein. Typically, the endoscopic video system and the accompanying endoscopic tool are each inserted into the cavity usually through small incisions in the patient's skin. The endoscopic video system is generally equipped with a light source to illuminate the cavity and an image transmission unit to transfer images of the cavity captured by the objective lens system to the video monitor so that a user of the endoscopic video system can view the images.

The video monitor usually displays a 2D video image of the cavity of the patient. Because the endoscopic video system and the endoscopic tool are often inserted into the cavity at different incisions in the patient's skin, the 2D video image view angle aligns only with the endoscopic video system, and not with the endoscopic tool. A problem exists that it is difficult for a surgeon using the endoscopic video system and the endoscopic tool to accurately determine a position of the endoscopic tool relative to objects provided in the viewable cavity. For example, if the endoscopic tool were configured as a clip applier, and the surgeon were placing clips around an artery along the length of the artery at spaced intervals, the lack of visibility (at the site of the clip placement) hinders the ability of the surgeon to properly position a clip relative to a previously positioned clip. In fact, a surgeon viewing the video monitor to observe the movements of the clip applier in the cavity may accidentally place a clip too far from or too close to the previously positioned clip, or the surgeon may even accidentally cause the clip to overlap the previously positioned clip. Such accidental placement of the clip may damage the clip applier and the clips, and may even cause injury to the patient.

SUMMARY OF THE INVENTION

Accordingly, a feature of the present invention overcomes the drawbacks associated with existing endoscopic video systems. In this regard, a non-limiting feature of the present disclosure provides an endoscopic video system that includes at least a first and a second video imaging system to provide an enhanced multi-angled view of the cavity of the patient during a medical procedure, to enhance the accuracy and the safety of the medical procedure, and to prevent damage to the endoscopic video system and the accompanying endoscopic tool, as well as to ensure the health and safety of the patient.

According to a non-limiting feature of the present disclosure, an endoscopic video system for visualizing an internal body cavity is provided. The endoscopic video system may include a first instrument and a second instrument. The first instrument may include a light configured to illuminate the cavity, and a first camera configured to capture first images of the illuminated cavity. The second instrument may include a surgical tool configured to perform a surgical procedure, and a second camera configured to capture second images of the illuminated cavity. The endoscopic video system also may include a video control unit configured to receive the captured first and second images, and a video display configured to display the captured first and second images transmitted from the video control unit.

According to another non-limiting feature of the endoscopic video system, the first instrument may also include a first image transmission unit that includes a first image coupler and a first camera head to receive and to transmit the first images to the video control unit.

According to yet another non-limiting feature of the endoscopic video system, the second instrument may also include a hand piece and a rotatable shaft connected to a distal end of the hand piece and extending in an axial direction from the hand piece, and configured for insertion into the cavity of the body.

Accordingly to still another non-limiting feature of the endoscopic video system, the surgical tool may include a pair of jaws provided at a distal end of the rotatable shaft and may be configured to apply a clip positioned between the pair of jaws.

According to a non-limiting feature, the rotatable shaft may house the second camera, and wherein the second camera includes an imaging scope extending from the hand piece to the pair of jaws in the axial direction along an interior space of the rotatable shaft.

According to another non-limiting feature of the endoscopic video system, the imaging scope may include an objective lens system provided at a distal end thereof, and a second image transmission unit including a second image coupler and a second camera head provided at a proximal end thereof, wherein the second image transmission unit receives and transmits the second images to the video control unit.

According to yet another non-limiting feature of the endoscopic video system, the imaging scope may include an optical fiber.

According to still another non-limiting feature of the endoscopic video system, the optical fiber may be secured to a bearing provided in the hand piece such that the objective lens system and the optical fiber rotate with the pair of jaws without axially twisting the optical fiber.

According to a non-limiting feature of the endoscopic video system, the optical fiber may include a service loop to reduce the stress on the optical fiber when the optical fiber rotates with the pair of jaws.

According to another non-limiting feature of the endoscopic video system, the second camera may include an objective lens system having an optical axis, and the optical axis may be generally parallel to an axial length of the second instrument.

According to yet another non-limiting feature of the endoscopic video system, the hand piece may include a handle portion, and a trigger pivotally connected to the handle portion and configured to actuate the surgical tool.

According to still another non-limiting feature of the endoscopic video system, the hand piece may be configured to accept a cartridge including clips, which is insertable into the hand piece, and wherein the cartridge is extendable through the rotatable shaft such that a clip from the cartridge is positioned between the pair of jaws.

According to a non-limiting feature of the endoscopic video system, the hand piece may include an adjuster configured to rotate the rotatable shaft about an axial length of the second instrument and to rotatably adjust the orientation of the pair of jaws.

According to another non-limiting feature of the endoscopic video system, the hand piece may include an adjuster configured to rotate the rotatable shaft independent of the rotation of the imaging scope secured to the bearing.

According to yet another non-limiting feature of the endoscopic video system, the second instrument may be a clip applier.

According to still another non-limiting feature of the endoscopic video system, the imaging scope may include a first section and a second section, wherein the first section is provided along the rotatable shaft and the second section is provided along the hand piece.

According to a non-limiting feature of the endoscopic video system, the video control unit may include a first camera controller electrically connected to the first instrument through a first image transmission unit, a second camera controller electrically connected the second instrument through a second image transmission unit, and a picture-in-picture converter electrically connected to the first camera controller, the second camera controller, and the video display, wherein the picture-in-picture converter communicates with the video display such that the first and second images are displayed simultaneously.

According to another non-limiting feature of the endoscopic video system, the picture-in-picture converter may include a processor configured to adjust a relative size of the first and second images displayed on the video display.

According to yet another non-limiting feature of the endoscopic video system, the picture-in-picture converter may include a processor configured to adjust a relative position of the first and second images displayed on the video display.

According to still another non-limiting feature of the endoscopic video system, the picture-in-picture converter may include a processor configured to display at least one of the first and second images, and a third image that is not of the illuminated cavity, on the video display.

According to a non-limiting feature of the endoscopic video system, the first image may be a perspective view of the illuminated cavity, and the second image may be a perspective view of a target site of the surgical procedure, and wherein the first and second images are simultaneously displayed on the video display.

According to another non-limiting feature of the endoscopic video system, the perspective view of the target site of the surgical procedure is generally parallel to an axial length of the surgical tool.

According to a non-limiting feature of the present application, a clip applier is provided. The clip applier may include a hand piece, a tool end assembly including a frame and a pair of jaws, wherein the tool end assembly extends from the hand piece in an axial direction, a rotatable shaft extending from the hand piece and surrounding the tool end assembly, wherein the pair of jaws are provided at a distal end of the rotatable shaft and configured to apply a clip around at least one object, and an imaging scope fixedly attached to the frame and extending in the axial direction along an interior space of the rotatable shaft.

According to another non-limiting feature of the clip applier, the imaging scope may include an objective lens system provided at a distal end of the frame to capture images in a direction generally parallel to an axial length of the tool end assembly, and an image transmission unit including an image coupler and a camera head provided at a proximal end of the imaging scope to receive and to transmit the images captured by the objective lens system to a video display.

According to yet another non-limiting feature of the clip applier, the pair of jaws and the imaging scope, which are fixedly attached to the tool end assembly, rotate with the rotatable shaft.

According to still another non-limiting feature of the clip applier, the clip applier may include a collar connected at a distal end of the hand piece, a mounting brace provided at an upper end of the hand piece, and a hood extending from an upper end of the collar to an upper end of the mounting brace so as to define an enclosure between the hood and at least a portion of the hand piece.

According to a non-limiting feature of the clip applier, the imaging scope may include a first section and a second section, wherein the first section is provided along the rotatable shaft and the second section is provided along the hand piece.

According to another non-limiting feature of the clip applier, the imaging scope may include a first section and a second section, wherein the first section is provided along the rotatable shaft and the second section is provided within the enclosure of the hood.

According to yet another non-limiting feature of the clip applier, the collar may include an opening that allows the second section of the imaging scope to connect with the first section of the imaging scope along the rotatable shaft.

According to still another non-limiting feature of the clip applier, the hand piece may include a handle portion, a trigger pivotally connected to the handle portion and configured to actuate the pair of jaws, and an aperture configured to accept a cartridge including clips provided at a proximal side of the hand piece opposite the rotatable shaft, wherein the cartridge is extendable through the rotatable shaft such that a clip from the cartridge is positioned between the pair of jaws.

According to a non-limiting feature of the clip applier, the imaging scope may include an optical fiber.

According to another non-limiting feature of the clip applier, the hand piece may include a bearing extending through the mounting brace, wherein a proximal end of the optical fiber is secured to the bearing such that the optical fiber rotates relative to the mounting brace to prevent twisting of the optical fiber.

According to yet another non-limiting feature of the clip applier, the pair of jaws and the optical fiber are fixedly attached to the tool end assembly and rotate with the rotatable shaft, and the optical fiber includes a service loop to reduce the stress on the optical fiber when the optical fiber rotates with the pair of jaws.

According to still another non-limiting feature of the clip applier, the hand piece may include an adjuster to rotate the rotatable shaft about an axial length of the tool end assembly and to rotatably adjust the orientation of the pair of jaws to apply the clip around at least one object.

BRIEF DESCRIPTION OF THE DRAWINGS

The present disclosure provides a detailed description that follows by reference to the noted drawings by way of non-limiting examples, in which like reference numerals represent similar parts throughout several views of the drawings, and in which.

DETAILED DESCRIPTION OF THE EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

Accordingly, the present disclosure relates to an endoscopic video system for visualizing an internal body cavity, including an endoscopic instrument, such as a clip applier, capable of being incorporated into the endoscopic video system. However, it is contemplated that other known endoscopic instruments may also be implemented into the disclosed endoscopic video system.

The Endoscopic Video System

Figure 1:
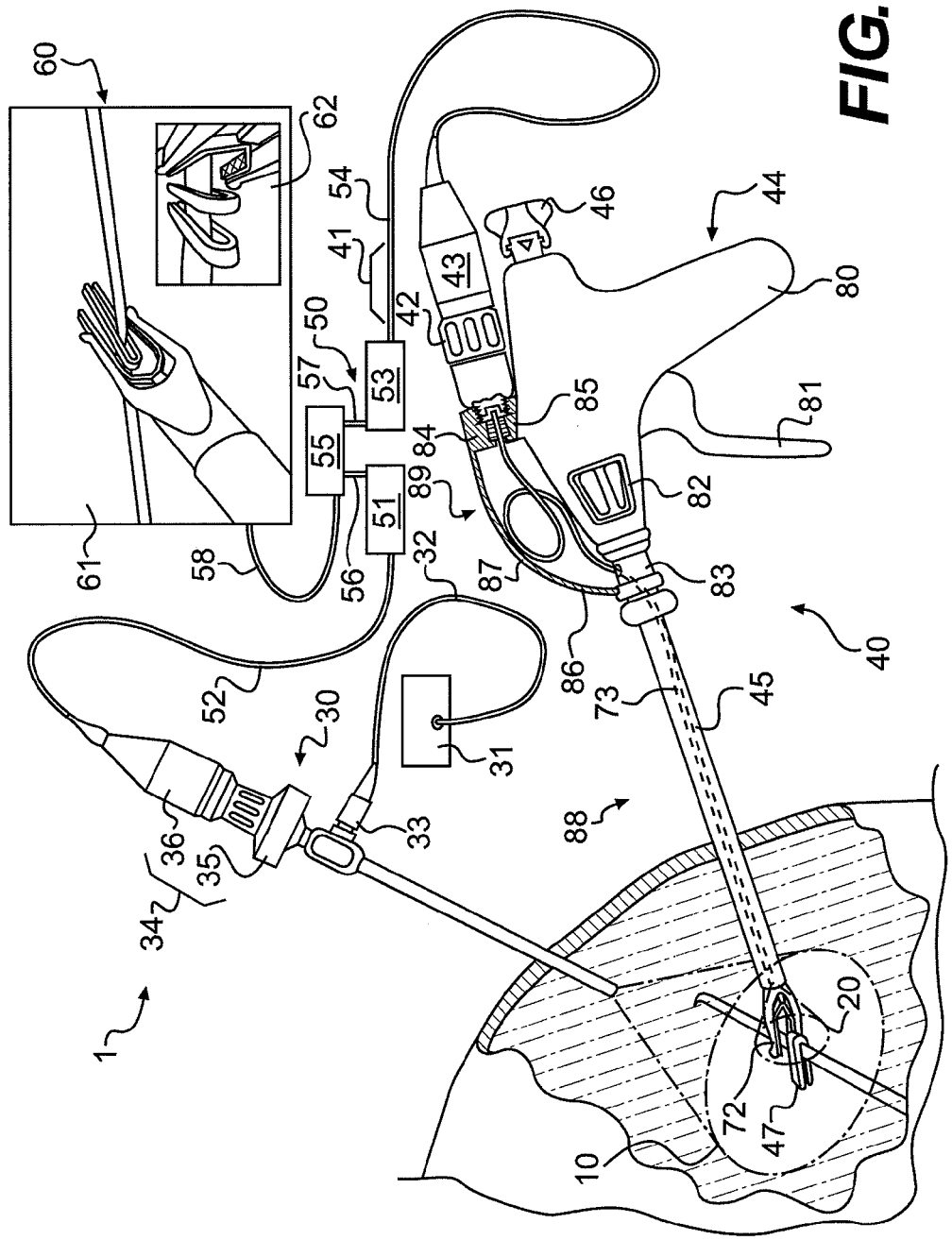
FIG. 1 is a perspective view of an endoscopic video system for use in a medical procedure according to a non-limiting feature of the present disclosure.

FIG. 1 shows an endoscopic video system (1) for visualizing an internal body cavity (10) and a target site (20) of the body cavity (10). The endoscopic video system (1) generally includes a first instrument (30) to illuminate the body cavity (10) and/or to capture images of the body cavity (10), a second instrument (40) to perform a medical procedure and to capture images of a portion of the illuminated cavity (10) including the target site (20), and a video control unit (50) to receive the captured images from the first and second instruments and to transmit them to a video display (60) for viewing during a medical procedure.

More particularly, the first instrument (30) may include a light source (31) configured to illuminate the cavity (10), and a first camera configured to capture first images (61) of the illuminated cavity (10) including the target site (20). The light source (31) may be connected to the first instrument (30) via a cable (32) at a port (33), as shown in FIG. 1. Alternatively, the light source (31) may be integrally attached to the first instrument (30) to illuminate the cavity (10). For example, the light source (31) may be provided along an axial length of the first instrument (30).

In embodiments, the cable (32) may be configured as a fiber optic bundle serving as a light guide. Alternatively, the cable (32) may be replaced with any other known connector suitable for light transmission. The first camera may be configured as an objective lens system including a CMOS, CCD or other type of image sensor for converting image light into electrical signals for transmission to the video display (60), such as a computer monitor or a video screen. The first camera also includes a first image transmission unit (34) including a first image coupler (35) and a first camera head (36) to receive and to transmit the first images (61) to the video control unit (50). The video control unit (50) processes the images from the first camera for display on the video display (60).

The second instrument (40) may include a surgical tool (72) configured to perform a surgical procedure, and a second camera configured to capture second images (62) of the illuminated cavity (10). In embodiments and similar to placement of the light source (31), as described above, a light source may be provided with the second instrument (40), and either connected to the second instrument (40) via a cable, or integrally attached to the second instrument (40), such as along the axial length of the second instrument (40), to further illuminate the cavity at the target site (20), and to enhance the visual clarity of the viewable area. In embodiments, the surgical tool (72) may be configured as an ablator, a scalpel, a clip applier, scissors, a clamp, forceps, cauterizers, or any other suitable surgical tool for use with an endoscope. In addition, the term "image," as used through the specification, may be defined as anything displayable on the video display (60), and thus images shown on the video display (60) should not be limited to the images captured by the first and second cameras.

Similar to the configuration of the first camera, the second camera also includes an objective lens system including CMOS, CCD or other type of image sensor for converting image light into electrical signals for transmission to the video display (60). The second camera further includes a second image transmission unit (41) including a second image coupler (42) and a second camera head (43) to receive and to transmit the second images (62) to the video control unit (50) where the images are processed for display on the video display (60).

In addition, the objective lens system of the second camera has an optical axis, which is generally parallel to an axial length of the surgical tool (72). This configuration enables the second camera to provide a view of the internal cavity (10) and the target site (20) that is different from the view produced by the first camera. This view, referred to herein as a "tool's eye view," provides an additional perspective of the internal cavity (10) and the target site (20), which improves the visibility of the movements of the surgical tool (72) at the target site (20) relative to other objects in the illuminated cavity (10). The enhanced visibility improves the accuracy and safety of the procedure, and reduces the time required for the procedure.

As noted above, the video control unit (50) is configured to receive the captured first and second images (61,62), and the video display (60) is configured to display the images (61,62) transmitted from the video control unit (50). Further, the video control unit (50) includes a first instrument camera controller (51) electrically connected to the first camera through the first image transmission unit (34) via a cable (52), a second instrument camera controller (53) electrically connected to the second camera through the second image transmission unit (41) via a cable (54), and a picture-in-picture converter (55) that is electrically connected to each of the first and second instrument camera controllers (51,53) via cables (56,57). The video control unit (50) is also electrically connected to the video display (60) via cable (58).

The picture-in-picture converter (55) communicates with the video display (60) such that the first and second images (61,62) may be displayed singularly or simultaneously. It is contemplated that the picture-in-picture converter (55) may electrically connect to additional camera controllers (and their respective cameras) to capture additional images in the illuminated body cavity (10). In addition, the picture-in-picture converter (55) may also connect to other devices, such as an EKG machine, a thermometer, or any other device capable of communicating with (and transmitting image or other data to) the picture-in-picture converter (55). Such connections enhance the operability of the endoscopic video system (1) and improve the ease-of-use of the system during a given medical procedure.

Further, while the camera controllers (51,53) and the video display (60) are electrically connected to the picture-in-picture converter (55) via cables (56,57,58), it is also contemplated that the various cable connections described herein may be replaced to include other known data transmission mechanisms, such as wireless connections and infrared connections.

The picture-in-picture converter (55) also includes a processor configured to adjust a relative size and a relative position of the first and second images (61,62) displayed on the video display (60) so that the images may be displayed in various arrangements suitable to the preferences of the person using the endoscopic video system (1). In this regard, the picture-in-picture converter (55) may be associated with a computer program that allows the user to interface with the endoscopic video system (1) and set (or adjust) user preferences.

The processor may also be configured to display at least one of the first and second images, and a third image (or more) that is not of the illuminated cavity (10) on the video display (60). The third image may be, for example, an EKG monitor, a brightness detector, a temperature reading, a timer, or any other image that may be useful to the surgeon during the medical procedure. In addition, the images may be shown individually or simultaneously. When shown simultaneously, the images on the video display (60) may be overlapped, spaced from one another or superimposed on one another depending on the preferences of the surgeon.

It is noted that the first image (61) may be a perspective view of the illuminated cavity (10) showing the surgical tool (72) and the target site (20) for the medical procedure. Meanwhile, the second image (62) may be a perspective view of the target site (20) of the medical procedure at the surgical tool (72), as shown in FIG. 1. In embodiments, the perspective view, i.e., also referred to as the tool's eye view, of the target site (taken at the surgical tool (72)) is generally parallel to the axial length of the surgical tool (72). Additionally, it is contemplated that the images may be thermal imaging images, color images, black and white images, and other images suitable for observation on the video display (60).

Clip Applier

In embodiments, the second instrument (40) may be configured as a clip applier, and the clip applier may be incorporated into the endoscopic video system (1) discussed above. The clip applier will now be described in detail with reference to FIGS. 1-3.

Figure 2:
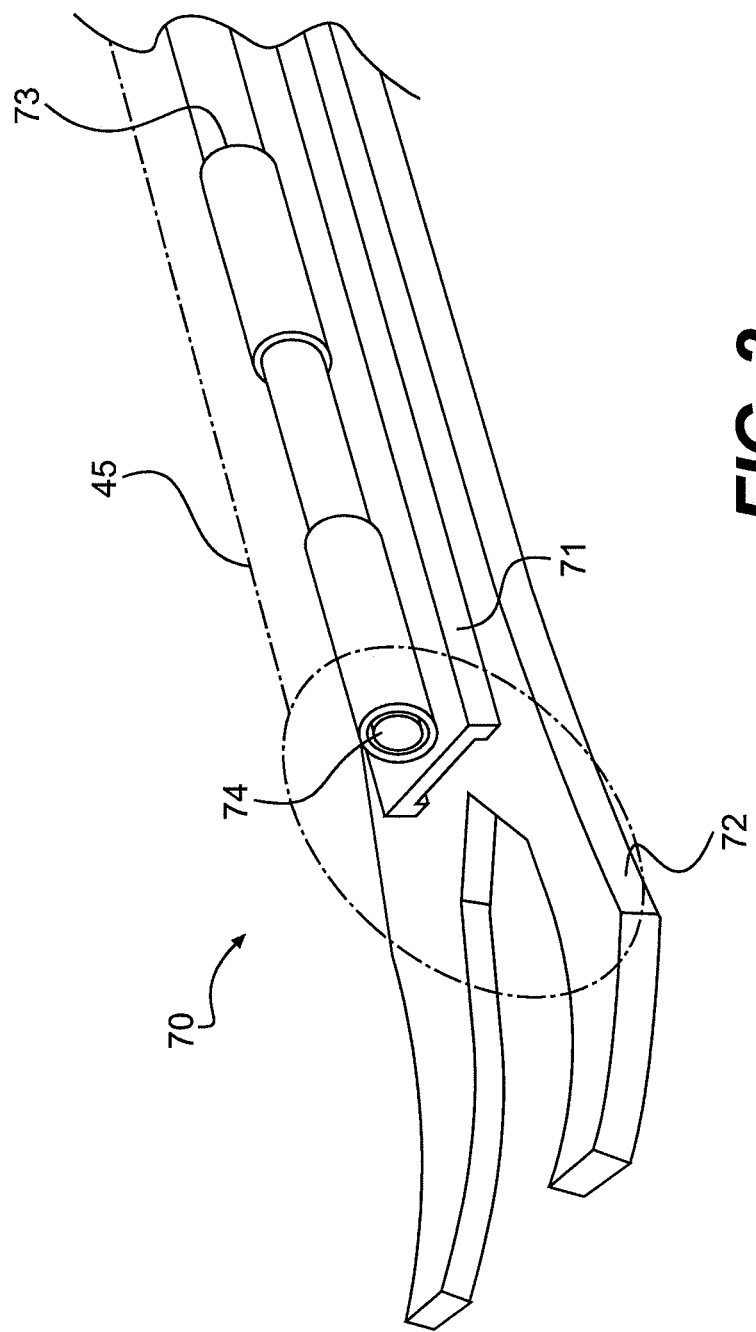
FIG. 2 is a partial perspective view of a distal end of an endoscopic tool including an imaging scope fixedly attached thereto so as to capture images in a direction generally parallel to an axial length of the endoscopic instrument according to a non-limiting feature of the present disclosure.

As shown in FIGS. 1 and 2, the clip applier (40) may include a hand piece (44), a rotatable shaft (45), and a tool end assembly (70) including a frame (71) configured to receive a cartridge (46) of stacked clips and a pair of jaws (72). The tool end assembly (70) extends from the hand piece (44) in an axial direction, and the rotatable shaft (45) extends from the hand piece (44) in the axial direction and surrounds the tool end assembly (70). The pair of jaws (72) is provided at a distal end of the rotatable shaft (45) and is configured to apply a clip (47) around at least one object.

The clip applier (40) also includes an imaging scope (73), i.e., similar to the second camera discussed above, that is attached to the frame (71) and extends in the axial direction along an interior space of the rotatable shaft (45). As shown in FIG. 2, the imaging scope (73), includes an objective lens system (at 74) and is connected to the second image transmission unit (41). At least a portion of the imaging scope (73) is housed by the rotatable shaft (45), while the other portion is associated with the hand piece (44). As also shown, the imaging scope (73) and the pair of jaws (72) are attached to the frame (71) and rotate with the rotation of the rotatable shaft (45). In this regard, the imaging scope (73) may be welded or clamped at spaced intervals along the axial length of the frame (71). In addition, the imaging scope (73) may be a micro flexible optical fiber having a 10 k fiber.

In embodiments, the hand piece (44) includes a handle portion (80) and a trigger (81) pivotally connected to the handle portion (80). The trigger (81) is configured to actuate the pair of jaws (72). The hand piece (44) also includes an aperture configured to accept the cartridge (46) of stacked clips. The aperture extends through the axial length of the hand piece (44) so that the cartridge (46) can be inserted into the aperture from a proximal side of the hand piece (44) towards the pair of jaws (72) provided at the distal end of the clip applier (40). Further, the cartridge (46) is configured to extend through the aperture of the hand piece (44) and through the rotatable shaft (45) via a cartridge receptacle formed in the frame (71).

While the cartridge (46) is described as being loaded at the proximal side of the hand piece (44), it is also contemplated that the cartridge (46) may also be loaded into the hand piece (44) via, for example, an aperture located at a side location, an anterior side or a posterior side of the hand piece (44). Alternatively, the cartridge (46) may also be loaded into the hand piece (44) via a slidable (or hinged) loading drawer provided at any one of the above-noted locations. In embodiments, it is further contemplated that the cartridge (46) may be pre-loaded with the hand piece (44), and not removable.

The hand piece (44) further includes an adjuster (82) that is configured to rotate the rotatable shaft (45) about its central axis and to rotatably adjust the orientation of the pair of jaws (72) to apply the clip (47) around at least one object. Thus, in operation, the user manipulates the adjuster (82) so as to rotate the pair of jaws (72) into position to apply the clip (47) to an object in the cavity (10) at the target site (20). When the trigger (81) is manipulated, the clip (47) is discharged from the cartridge (46) and positioned between the pair of jaws (72) to be applied to the object at the target site (20). In this regard, the pair of jaws (72) may be configured either to crimp an elastically-biased open clip around the object, or to open an elastically-biased closed clip for placement around the object. It is further contemplated that the clip applier (40) may also be configured to apply staples or may function to grasp objects for removal from or adjustment within the cavity (10). In other words, the clip applier (40) may be used for purposes other than to apply a clip or a staple for increased functionality of the device.

The clip applier (40) still further includes a collar (83) connected at a distal end of the hand piece (44), a mounting brace (84) including a bearing (85) extending therethrough provided at an upper end of the hand piece (44), and a hood (86) extending from an upper end of the collar (83) to an upper end of the mounting brace (84) so as to define an enclosure between the hood (86) and at least a portion of the hand piece (44). The collar (83) connects the rotatable shaft (45) to the hand piece (44), and the mounting brace (84) houses the bearing (85). As noted above, the bearing (85) extends through the mounting brace (84), and a proximal end of the optical fiber is secured to the bearing (85) such that the optical fiber rotates relative to the mounting brace and connects with the second image transmission unit (41).

The hood (86) may be any shape and material suitable for housing a service loop (87) of the imaging scope (73), which provides additional slack to address twisting experienced by the optical fiber during operation of the rotatable shaft (45).

The hood (86) also protects the service loop (87) from contamination and prevents damage to the optical fiber. It is contemplated that the hood (86) may further be configured to be removable for access to the service loop (87) or for repair to a portion of the clip applier (40). In this regard, it is noted that the clip applier (40) may be disposable or reusable.

As shown in FIG. 1, the optical fiber (i.e., the imaging scope) is secured to the bearing (85). The optical fiber is secured to the bearing (48) such that the objective lens system (at 74) and the optical fiber rotate with the rotation of the pair of jaws (72) while limiting the axial twisting experienced by the optical fiber during rotation of the rotatable shaft (45). That is, the bearing (48) aids in preventing potential breakage of the optical fiber due to excessive twisting along the rotatable shaft (45) when the user manipulates the adjuster (82). It is noted that the rotation of the imaging scope (73) along the rotatable shaft (45) is independent of the rotation of the imaging scope (73) secured at the bearing (85).

The imaging scope (73) can be viewed as having a first section (88) and a second section (89), which includes the service loop (87). The first section (88) is provided along the rotatable shaft (45) and the second section (89) is provided along the hand piece (44) within the enclosure defined by the hood (86). As previously noted, the first section (88) of the imaging scope (73) may be welded or clamped at spaced intervals along the frame (71). The second section (89) (including the service loop (87) secured to the bearing (85)) reduces the stress (including the axial twisting) experienced by the imaging scope (73) when the optical fiber provided along the tool end assembly (70) rotates with the rotation of the pair of jaws (72) and the rotatable shaft (45).

Figure 3:
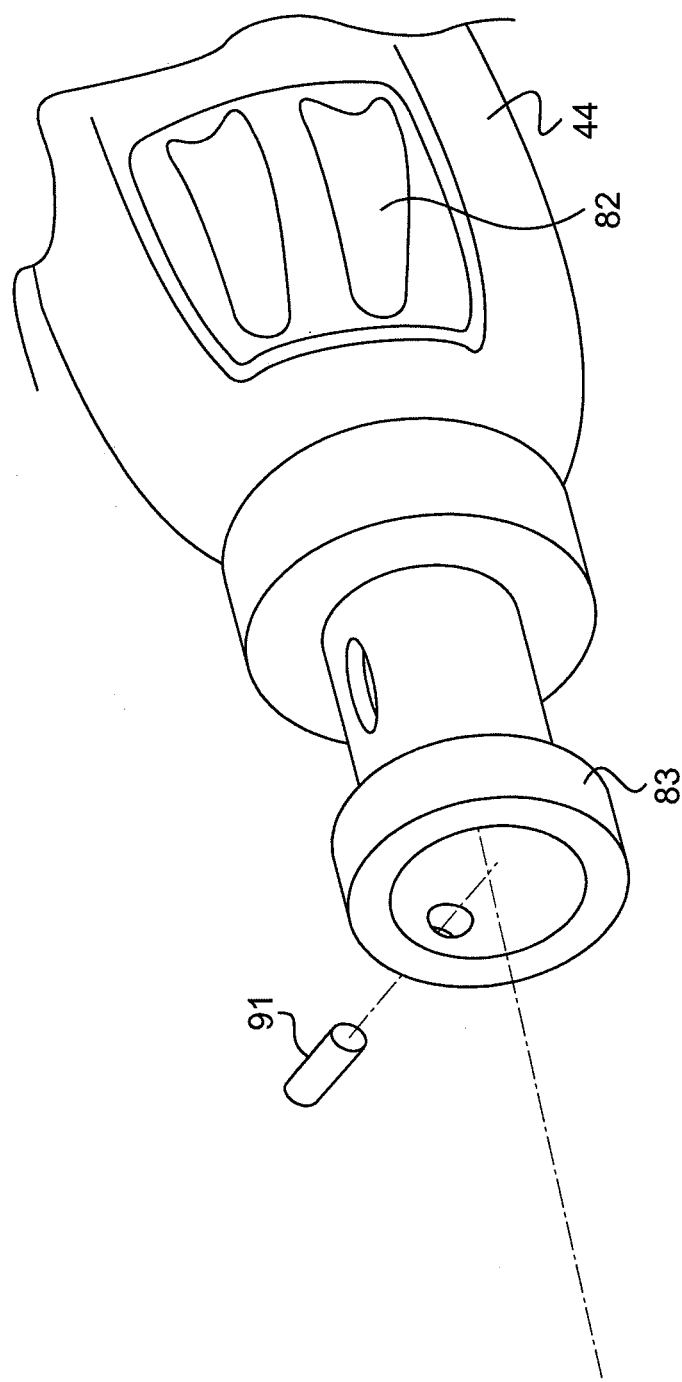
FIG. 3 is a partial perspective view of a collar disposed at a distal end of a hand piece according to a non-limiting feature of the present disclosure.

As shown in FIG. 2, the first section (88) and the second section (89) are connected to one another via an opening (90) in the collar (83). As shown in FIG. 3, the opening (90) allows the service loop (87) to extend and to retract into the first section (88) without being exposed to an external environment. This configuration not only addresses the twisting concerns, it also prevents contamination to the imaging scope (73) and protects the imaging scope (73) from being damaged or mishandled. In addition, the collar (83) may include a stop pin (91) provided at a side of the collar (83) as an additional safety mechanism that limits the amount of twisting experienced by the optical fiber and to prevent the optical fiber from being twisted to the point of fracture.

Accordingly, the endoscopic video system as discussed in detail above, provides users an enhanced view of the area targeted for a given medical procedure. As a result, the accuracy and the safety of the medical procedure is improved, the risk of damage to the endoscopic video system and the accompanying endoscopic tool is greatly reduced, and the health and safety of the patient is ensured.

Although the invention has been described with reference to several exemplary embodiments, which can be combined in any suitable manner, it is understood that the words that have been used are words of description and illustration, rather than words of limitation. Changes may be made within the purview of the appended claims, as presently stated and as amended, without departing from the scope and spirit of the invention in its aspects. Although the invention has been described with reference to particular means, materials and embodiments, the invention is not intended to be limited to the particulars disclosed. Rather, the invention extends to all functionally equivalent structures, methods and uses such as are within the scope of the appended claims.

What is claimed is:

1. An endoscopic video system for visualizing an internal body cavity, comprising:
   a first instrument comprising:
      a light configured to illuminate the cavity; and
      a first camera configured to capture first images of the illuminated cavity;
   a second instrument comprising:
      a surgical tool configured to perform a surgical procedure; and
      a second camera configured to capture second images of the illuminated cavity;
   a video control unit configured to receive the captured first and second images; and
   a video display configured to display the captured first and second images transmitted from the video control unit,
   wherein the second instrument further comprises a hand piece and a rotatable shaft connected to a distal end of the hand piece and extending in an axial direction from the hand piece, and configured for insertion into the cavity of the body,
   wherein the surgical tool comprises a pair of jaws provided at a distal end of the rotatable shaft, and
   wherein the rotatable shaft houses the second camera, and wherein the second camera includes an imaging scope extending from the hand piece to the pair of jaws in the axial direction along an interior space of the rotatable shaft.

2. The endoscopic video system of claim 1, wherein the first instrument further comprises a first image transmission unit that includes a first image coupler and a first camera head to receive and to transmit the first images to the video control unit.

3. The endoscopic video system of claim 1, wherein the pair of jaws is configured to apply a clip positioned between the pair of jaws.

4. The endoscopic video system of claim 1, wherein the imaging scope includes an objective lens system provided at a distal end thereof, and a second image transmission unit including a second image coupler and a second camera head provided at a proximal end thereof, wherein the second image transmission unit receives and transmits the second images to the video control unit.

5. The endoscopic video system of claim 1, wherein the second camera includes an objective lens system having an optical axis, and wherein the optical axis is generally parallel to an axial length of the second instrument.

6. The endoscopic video system of claim 1, wherein the hand piece includes a handle portion, and a trigger pivotally connected to the handle portion and configured to actuate the surgical tool.

7. The endoscopic video system of claim 1, wherein the second instrument is a clip applier.

8. The endoscopic video system of claim 1, wherein the imaging scope includes a first section and a second section, wherein the first section is provided along the rotatable shaft and the second section is provided along the hand piece.

9. The endoscopic video system of claim 1, wherein the video control unit includes:
   a first camera controller electrically connected to the first instrument through a first image transmission unit;
   a second camera controller electrically connected the second instrument through a second image transmission unit; and
   a picture-in-picture converter electrically connected to the first camera controller, the second camera controller, and the video display, wherein
   the picture-in-picture converter communicates with the video display such that the first and second images are displayed simultaneously.

10. The endoscopic video system of claim 1, wherein the first image is a perspective view of the illuminated cavity, and the second image is a perspective view of a target site of the surgical procedure, and wherein the first and second images are simultaneously displayed on the video display.

11. The endoscopic video system of claim 3, wherein the hand piece is configured to accept a cartridge including clips, which is insertable into the hand piece, wherein the cartridge is extendable through the rotatable shaft such that a clip from the cartridge is positioned between the pair of jaws.

12. The endoscopic video system of claim 3, wherein the hand piece includes an adjuster configured to rotate the rotatable shaft about an axial length of the second instrument and to rotatably adjust the orientation of the pair of jaws.

13. The endoscopic video system of claim 4, wherein the imaging scope comprises an optical fiber.

14. The endoscopic video system of claim 9, wherein the picture-in-picture converter includes a processor configured to adjust a relative size of the first and second images displayed on the video display.

15. The endoscopic video system of claim 9, wherein the picture-in-picture converter includes a processor configured to adjust a relative position of the first and second images displayed on the video display.

16. The endoscopic video system of claim 9, wherein the picture-in-picture converter includes a processor configured to display at least one of the first and second images, and a third image that is not of the illuminated cavity, on the video display.

17. The endoscopic video system of claim 10, wherein the perspective view of the target site of the surgical procedure is generally parallel to an axial length of the surgical tool.

18. The endoscopic video system of claim 13, wherein the optical fiber is secured to a bearing provided in the hand piece such that the objective lens system and the optical fiber rotate with the pair of jaws without axially twisting the optical fiber.

19. The endoscopic video system of claim 13, wherein the optical fiber includes a service loop to reduce the stress on the optical fiber when the optical fiber rotates with the pair of jaws.

20. The endoscopic video system of claim 18, wherein the hand piece includes an adjuster configured to rotate the rotatable shaft independent of the rotation of the imaging scope secured to the bearing.

21. A clip applier comprising:
a hand piece;
a tool end assembly including a frame and a pair of jaws, wherein the tool end assembly extends from the hand piece in an axial direction,
a rotatable shaft extending from the hand piece and surrounding the tool end assembly, wherein the pair of jaws are provided at a distal end of the rotatable shaft and configured to apply a clip around at least one object; and
an imaging scope fixedly attached to the frame and extending in the axial direction along an interior space of the rotatable shaft.

22. The clip applier of claim 21, wherein the imaging scope includes an objective lens system provided at a distal end of the frame to capture images in a direction generally parallel to an axial length of the tool end assembly, and an image transmission unit including an image coupler and a camera head provided at a proximal end of the imaging scope to receive and to transmit the images captured by the objective lens system to a video display.

23. The clip applier of claim 21, wherein the pair of jaws and the imaging scope, which are fixedly attached to the tool end assembly, rotate with the rotatable shaft.

24. The clip applier of claim 21 further including:
a collar connected at a distal end of the hand piece;
a mounting brace provided at an upper end of the hand piece; and
a hood extending from an upper end of the collar to an upper end of the mounting brace so as to define an enclosure between the hood and at least a portion of the hand piece.

25. The clip applier of claim 21, wherein the imaging scope includes a first section and a second section, wherein the first section is provided along the rotatable shaft and the second section is provided along the hand piece.

26. The clip applier of claim 21, wherein the hand piece includes:
a handle portion;
a trigger pivotally connected to the handle portion and configured to actuate the pair of jaws; and
an aperture configured to accept a cartridge including clips provided at a proximal side of the hand piece opposite the rotatable shaft, wherein the cartridge is extendable through the rotatable shaft such that a clip from the cartridge is positioned between the pair of jaws.

27. The clip applier of claim 21, wherein the hand piece includes an adjuster to rotate the rotatable shaft about an axial length of the tool end assembly and to rotatably adjust the orientation of the pair of jaws to apply the clip around at least one object.

28. The clip applier of claim 24, wherein the imaging scope includes a first section and a second section, wherein the first section is provided along the rotatable shaft and the second section is provided within the enclosure of the hood.

29. The endoscopic video system of claim 24, wherein the imaging scope comprises an optical fiber.

30. The clip applier of claim 25, wherein the collar includes an opening that allows the second section of the imaging scope to connect with the first section of the imaging scope along the rotatable shaft.

31. The clip applier of claim 29 further including a bearing extending through the mounting brace, and wherein a proximal end of the optical fiber is secured to the bearing such that the optical fiber rotates relative to the mounting brace to prevent twisting of the optical fiber.

32. The endoscopic video system of claim 29, wherein the pair of jaws and the optical fiber are fixedly attached to the tool end assembly and rotate with the rotatable shaft, and wherein the optical fiber includes a service loop to reduce the stress on the optical fiber when the optical fiber rotates with the pair of jaws.

* * * * *